United States Patent [19]
Heinemann et al.

[11] Patent Number: 6,031,107
[45] Date of Patent: Feb. 29, 2000

[54] FLUOROMETHOXYACRYLIC ACID DERIVATIVES AND THEIR USE AS PEST CONTROL AGENTS

[75] Inventors: Ulrich Heinemann, Leichlingen; Herbert Gayer, Monheim; Peter Gerdes, Aachen; Albrecht Marhold, Leverkusen; Uwe Stelzer, Burscheid; Ralf Tiemann, Leverkusen; Klaus Stenzel, Düsseldorf; Stefan Dutzmann, Langenfeld, all of Germany

[73] Assignee: Bayer Aktiengesellschaft, Leverkusen, Germany

[21] Appl. No.: 09/051,653

[22] PCT Filed: Oct. 7, 1996

[86] PCT No.: PCT/EP96/04344

§ 371 Date: Apr. 16, 1998

§ 102(e) Date: Apr. 16, 1998

[87] PCT Pub. No.: WO97/14687

PCT Pub. Date: Apr. 24, 1997

[30] Foreign Application Priority Data

Oct. 18, 1995 [DE] Germany ............... 195 38 790
Mar. 25, 1996 [DE] Germany ............... 196 11 653

[51] Int. Cl.$^7$ ............... C07D 285/08; C07D 417/04; C07D 307/12; C07D 309/12; A01N 43/836; C07C 69/734

[52] U.S. Cl. ............... 548/129; 514/361; 560/55
[58] Field of Search ............... 548/129; 514/361; 560/55

[56] References Cited

U.S. PATENT DOCUMENTS 5,438,066  8/1995  Matthews ............... 514/361

FOREIGN PATENT DOCUMENTS

WO 94 10159  5/1994  WIPO.
WO 95 17376  6/1995  WIPO.

*Primary Examiner*—Floyd D. Higel
*Attorney, Agent, or Firm*—Norris, McLaughlin & Marcus, P.A.

[57] ABSTRACT

The invention relates to new fluoromethoxyacrylic acid derivatives, a process for their preparation and their use as pesticides, as well as to new intermediates and a plurality of processes for their preparation.

It has already been disclosed that certain fluoromethoxy-acrylic acid derivatives which are similar in constitution to the compounds described below have fungicidal properties (compare, for example, WO 9517376). The fungicidal action of these compounds, however, is unsatisfactory in many cases.

8 Claims, No Drawings

FLUOROMETHOXYACRYLIC ACID DERIVATIVES AND THEIR USE AS PEST CONTROL AGENTS

The invention relates to new fluoromethoxyacrylic acid derivatives, a process for their preparation and their use as pesticides, as well as to new intermediates and a plurality of processes for their preparation.

It has already been disclosed that certain fluoromethoxyacrylic acid derivatives which are similar in constitution to the compounds described below have fuigicidal properties (compare, for example, WO 9517376). The fungicidal action of these compounds, however, is unsatisfactory in many cases.

The new fluoromethoxyacrylic acid derivatives have now been found, of the general formula (I)

(I)

[Chemical structure: Ar-substituted thiadiazole connected via O to a phenyl ring bearing a =CH-O-CH$_2$F, COQ substituent]

in which
Ar represents substituted aryl and
Q represents optionally substituted alkoxy.

Aryl represents aromatic. mono- or polycyclic hydrocarbon rings, such as, for example, phenyl, naphthyl, anthranyl, phenanthryl, preferably phenyl or naphthyl, in particular phenyl.

The compounds according to the invention, if appropriate, can exist as mixtures of various possible isomeric forms. in particular of stereoisomers, such as, for example, E- and Z-. Both the E- and the Z-isomers, and also any desired mixtures of these isomers, are claimed.

The invention preferably relates to compounds of the formula (I), in which

Ar represents mono- to trisubstituted phenyl or optionally mono- to tetrasubstituted naphthyl, the possible substituents preferably being selected from the list below:
halogen, cyano, nitro; alkyl, alkoxy, alkylthio, alkylsulphinyl or alkylsulphonyl, each of which is straight-chain or branched and has 1 to 6 carbon atoms; alkenyl, alkenyloxy or alkinyloxy, each of which is straight-chain or branched and has 2 to 6 carbon atoms; halogenoalkyl, halogenoalkoxy, halogenoalkylthio, halogenoalkylsulphinyl or halogenoalkylsulphonyl, each of which is straight-chain or branched and has 1 to 6 carbon atoms and 1 to 13 identical or different halogen atoms; halogenoalkenyl or halogenoalkenyloxy, each of which is straight-chain or branched and has 2 to 6 carbon atoms and 1 to 11 identical or different halogen atoms; alkylamino, dialkylamino, alkylcarbonyl, alkylcarbonyloxy, alkoxycarbonyl, alkylsulphonyloxy, hydroximinoalkyl or alkoximinoalkyl, each of which is straight-chain or branched and has 1 to 6 carbon atoms in the individual alkyl moieties; alkylene or dioxyalkylene, each having 1 to 6 carbon atoms, and each of which is divalent and is optionally mono- or polysubstituted, identically or differently, by halogen and/or straight-chain or branched alkyl having 1 to 4 carbon atoms and/or straight-chain or branched halogenoalkyl having 1 to 4 carbon atoms and 1 to 9 identical or different halogen atoms; or cycloalkyl having 3 to 6 carbon atoms, and Q represents $C_1$–$C_6$-alkoxy which is optionally substituted by halogen or $C_1$–$C_4$-alkoxy.

In the definitions, the saturated or unsaturated hydrocarbon chains, such as alkyl, alkenyl or alkinyl, even linked to heteroatoms, such as in alkoxy, alkylthio or alkylamino, are each straight-chain or branched.

Halogen in general represents fluorine, chlorine, bromine or iodine, preferably fluorine, chlorine or bromine.

Cycloalkyl represents saturated, carbocyclic ring compounds, which optionally form a polycyclic ring system with other carbocyclic, fused or bridged rings.

The invention relates in particular to compounds of the formula (I), in which

Ar represents phenyl which is mono- or disubstituted, identically or differently, the possible substituents preferably being selected from the list below:
fluorine, chlorine, bromine, cyano, methyl, ethyl, n- or i-propyl, n-, i-, s- or t-butyl, cyclopropyl, methoxy, ethoxy, n- or i-propoxy, methylthio, ethylthio, n-or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, trifluoromethylthio, difluorochloromethylthio, trifluoromethylsulphinyl or trifluoromethylsulphonyl, methoxycarbonyl, ethoxycarbonyl, methoximinomethyl, ethoximinomethyl, methoximinoethyl, ethoximinoethyl, or methylenedioxy, ethylenedioxy, each of which is divalent and is optionally mono- to tetrasubstituted, identically or differently, by fluorine, chlorine, methyl, trifluoromethyl or ethyl, and Q represents methoxy or ethoxy.

The abovementioned radical definitions, given in general or in preferred ranges, apply both to the final products of the formula (I) and correspondingly to the starting substances or intermediates needed in each case for preparation.

These radical definitions can be combined with one another, i.e. also between the given ranges of preferred compounds, in any desired manner.

It has furthermore been found that the fluoromethoxyacrylic acid derivatives of the formula (I) have very good microbicidal properties and can be employed for the protection of plants against harmful organisms.

Surprisingly, the substances according to the invention show a better action than constitutionally similar, previously known active compounds of the same direction of action.

Finally, it has been found that both the new and the known fluoromethoxyacrylic acid derivatives of the general formula (Ia)

(Ia)

[Chemical structure: Ar$^1$-substituted thiadiazole connected via O to a phenyl ring bearing a =CH-O-CH$_2$F, COQ$^1$ substituent]

in which
Ar$^1$ represents optionally substituted aryl and $Q^1$ represents optionally substituted alkoxy,
are obtained when (process a) hydroxyaryl compounds of the general formula (II)

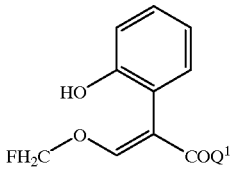
(II)

in which
$Q^1$ has the meaning indicated above,
are reacted with a thiadiazole derivative of the general formula (III)

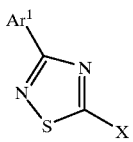
(III)

in which
$Ar^1$ has the meaning indicated above and
X represents halogen, alkylsulphonyl or arylsulphonyl,
if appropriate in the presence of an acid acceptor and if appropriate in the presence of a diluent.

It is to be regarded as particularly surprising here that the process according to the invention proceeds with considerably higher yields than the process known according to the prior art.

In process a) according to the invention, preferably compounds of the formula (Ia) are prepared in which
$Ar^1$ represents phenyl which is optionally mono- to trisubstituted or naphthyl which is optionally mono- to tetrasubstituted, the possible substituents preferably being selected from the list below:
halogen, cyano, nitro; alkyl, alkoxy, alkylthio, alkylsulphinyl or alkylsulphonyl, each of which is straight-chain or branched and has 1 to 6 carbon atoms; alkenyl, alkenyloxy or alkinyloxy, each of which is straight-chain or branched and has 2 to 6 carbon atoms; halogenoalkyl, halogenoalkoxy, halogenoalkylthio, halogenoalkylsulphinyl or halogenoalkylsulphonyl, each of which is straight-chain or branched and has 1 to 6 carbon atoms and 1 to 13 identical or different halogen atoms; halogenoalkenyl or halogenoalkenyloxy, each of which is straight-chain or branched and has 2 to 6 carbon atoms and 1 to 11 identical or different halogen atoms; alkylamino, dialkylamino, alkylcarbonyl, alkylcarbonyloxy, alkoxycarbonyl, alkylsulphonyloxy, hydroximinoalkyl or alkoximinoalkyl, each of which is straight-chain or branched and has 1 to 6 carbon atoms in the individual alkyl moieties; alkylene or dioxyalkylene, each having 1 to 6 carbon atoms, and each of which is divalent and is optionally mono- or polysubstituted, identically or differently, by halogen and/or straight-chain or branched alkyl having 1 to 4 carbon atoms and/or straight-chain or branched halogenoalkyl having 1 to 4 carbon atoms and 1 to 9 identical or different halogen atoms or cycloalkyl having 3 to 6 carbon atoms; and $Q^1$ represents $C_1$–$C_6$-alkoxy which is optionally substituted by halogen or $C_1$–$C_4$-alkoxy.

In particular, in process a) according to the invention, compounds of the formula (Ia) can be prepared in which
$Ar^1$ represents phenyl which is optionally mono- or disubstituted, identically or differently, the possible substituents preferably being selected from the list below:
fluorine, chlorine, bromine, cyano, methyl, ethyl, n- or i-propyl, n-, i-, s- or t-butyl, cyclopropyl, methoxy, ethoxy, n- or i-propoxy, methylthio, ethylthio, n-or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, trifluoromethylthio, difluorochloromethylthio, trifluoromethylsulphinyl or trifluoromethylsulphonyl, methoxycarbonyl, ethoxycarbonyl, methoximinomethyl, ethoxyiminomethyl, methoximinoethyl, ethoximinoethyl, or methylenedioxy, ethylenedioxy, each of which is divalent and optionally mono- to tetrasubstituted, identically or differently, by fluorine, chlorine, methyl, trifluoromethyl or ethyl, and $Q^1$ represents methoxy or ethoxy.

Formula (II) provides a general definition of the hydroxyaryl compounds needed as starting substances for carrying out process a) according to the invention. In this formula (II), $Q^1$ preferably or in particular has the meaning which has already been indicated as preferred or as particularly preferred in connection with the description of the compounds of the formula (Ia) according to the invention.

The hydroxyaryl compounds of the formula (II) are still unknown; as novel substances, they are a subject of the present application.

The hydroxyaryl compounds of the formula (II) are obtained (process b) when acetals of the formula (IV)

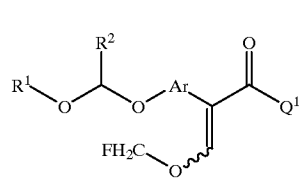
(IV)

in which
$R^1$ represents alkyl,
$R^2$ represents hydrogen or alkyl or
$R^1$ and $R^2$, together with the atoms to which they are bonded, represent a five- or six-membered, heterocyclic ring
$Q^1$ has the meaning indicated above,
are hydrolysed at temperatures from –20° C. to 120° C., preferably at temperatures from –10° C. to 80° C., if appropriate in the presence of a diluent, preferably of an aliphatic, alicyclic or aromatic hydrocarbon, such as, for example, petroleum ether, hexane, heptane, cyclohexane, methylcyclohexane, benzene, toluene, xylene or decalin; of a halogenated hydrocarbon, such as, for example, chlorobenzene, dichlorobenzene, dichloromethane, chloroform, tetrachloromethane, dichloroethane or trichloroethane: of an ether, such as diethyl ether, diisopropyl ether, methyl t-butyl ether, methyl t-amyl ether, dioxane, tetrahydrofuran, 1,2-dimethoxyethane, 1,2-diethoxyethane or anisole: of a ketone, such as acetone, butanone, methyl isobutyl ketone or cyclohexanone; of a nitrile, such as acetonitrile, propionitrile, n- or i-butyronitrile or benzonitrile; of an ester such as methyl acetate or ethyl acetate; of a sulphoxide, such as dimethyl sulphoxide; of a sulphone, such as sulpholane; of an alcohol, such as methanol, ethanol, n- or i-propanol, n-, i-, sec- or tert-butanol, ethanediol, propane-1,2-diol, ethoxyethanol, methoxyethanol, diethylene glycol monomethyl ether, diethylene glycol monoethyl ether, their mixtures with water or pure water, and if appropriate in the presence of an acid, preferably of an inorganic or organic protonic or Lewis acid, such as, for example, hydrochloric acid, sulphuric acid, phosphoric acid, formic acid, acetic acid, trifluoroacetic acid, methanesulphonic acid, trifluoromethanesulphonic acid, toluenesulphonic acid, boron trifluoride (also as etherate), boron tribromide, aluminium trichloride, zinc chloride, iron(III) chloride, antimony pentachloride, or alternatively of a polymeric acid such as, for example, an acidic ion exchanger, an acidic alumina or acidic silica gel.

Formula (IV) provides a general definition of the acetals needed as starting substances for carrying out process b) according to the invention. In this formula (IV), $Q^1$ preferably or in particular has the meaning which has already been indicated as preferred or as particularly preferred for $Q^1$ in connection with the description of the compounds of the formula (Ia) according to the invention. $R^1$ represents alkyl, preferably methyl or ethyl, $R^2$ represents hydrogen or alkyl, preferably methyl or ethyl, or $R^1$ and $R^2$, together with the atoms to which they are bonded, represent a five- or six-membered, heterocyclic ring, preferably tetrahydrofuryl or tetrahydropyrryl.

The acetals of the formula (IV) are still unknown; as new substances they are a subject of the present application.

The acetals of the formula (IV) are obtained when (process c) arylacetic acid derivatives of the formula (V)

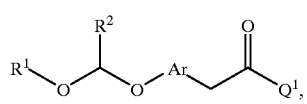

(V)

in which $R^1$, $R^2$ and $Q^1$ have the meanings indicated above, are first reacted with a formic acid derivative, such as, for example, methyl formate, carbon monoxide, a dialkylformamide acetal or a bis-dialkylaminoalkoxymethane, if appropriate in the presence of a diluent, preferably of an aliphatic, alicyclic or aromatic hydrocarbon, such as, for example, petroleum ether, hexane, heptane, cyclohexane, methylcyclohexane, benzene, toluene, xylene or decalin; of a halogenated hydrocarbon, such as, for example, chlorobenzene, dichlorobenzene, dichloromethane, chloroform, tetrachloromethane, dichloroethane or trichloroethane; of an ether, such as diethyl ether, diisopropyl ether, methyl t-butyl ether, methyl t-amyl ether, dioxane, tetrahydrofuran, 1,2-dimethoxyethane, 1,2-diethoxyethane or anisole; of a ketone, such as acetone, butanone, methyl isobutyl ketone or cyclohexanone, of a nitrile, such as acetonitrile, propionitrile, n- or i-butyronitrile or benzonitrile; of an ester such as methyl acetate or ethyl acetate; of an amide, such as N,N-dimethylformamide, N,N-dimethylacetamide, N-methylformanilide, N-methylpyrrolidone or hexamethylphosphoramide; of a sulphoxide, such as dimethyl sulphoxide; of a sulphone, such as sulpholane; of an alcohol, such as methanol, ethanol, n- or i-propanol, n-, i-, sec- or tert-butanol, ethanediol, propane- 1,2-diol, ethoxyethanol, methoxyethanol, diethylene glycol monomethyl ether or diethylene glycol monoethyl ether, and if appropriate in the presence of a basic catalyst, preferably of an alkaline earth metal or alkali metal or ammonium hydride, hydroxide, amide, alkoxide, acetate, carbonate or hydrogen carbonate, such as, for example, sodium hydride, sodium amide, sodium methoxide, sodium ethoxide, potassium tert-butoxide, sodium hydroxide, potassium hydroxide, ammonium hydroxide, sodium acetate, potassium acetate, calcium acetate, ammonium acetate, sodium carbonate, potassium carbonate, potassium hydrogen carbonate, sodium hydrogen carbonate or ammonium carbonate, or of a tertiary amine, such as trimethylamine, triethylamine, tributylamine N,N-dimethylaniline, N,N-dimethyl-benzylamine, pyridine, N-methylpiperidine, N-methylmorpholine, N,N-dimethylaminopyridine, diazabicyclooctane (DABCO), diazabicyclononene (DBN) or diazabicycloundecene (DBU), at temperatures from –20° C. to 120° C., preferably at temperatures from –10° C. to 80° C., and the enols thus obtained of the formula (VI)

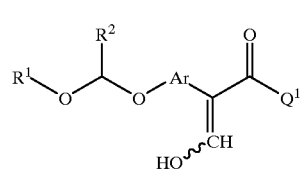

(VI)

in which $R^1$, $R^2$ and $Q^1$ have the meanings indicated above, are reacted, preferably without further working up, with fluorobromomethane or fluorochloromethane, if appropriate in the presence of a diluent, preferably of an aliphatic, alicyclic or aromatic hydrocarbon, such as, for example, petroleum ether, hexane, heptane, cyclohexane, methylcyclohexane, benzene, toluene, xylene or decalin; of a halogenated hydrocarbon, such as, for example, chlorobenzene, dichlorobenzene, dichloromethane, chloroform, tetrachloromethane, dichloroethane or trichloroethane; of an ether, such as diethyl ether, diisopropyl ether, methyl t-butyl ether, methyl t-amyl ether, dioxane, tetrahydrofuran, 1,2-dimethoxyethane, 1,2-diethoxyethane or anisole; of a ketone, such as acetone, butanone, methyl isobutyl ketone or cyclohexanone; of a nitrile, such as acetonitrile, propionitrile, n- or i-butyronitrile or benzonitrile; of an ester such as methyl acetate or ethyl acetate; of an amide, ,such as N,N-dimethylformamide, N,N-dimethylacetamide, N-methylformanilide, N-methylpyrrolidone or hexamethylphosphoramide; of a sulphoxide, such as dimethyl sulphoxide; of a sulphone, such as sulpholane; of an alcohol, such as methanol, ethanol, n- or i-propanol, n-, i-, sec- or tert-butanol, ethanediol, propane-1,2-diol, ethoxyethanol, methoxyethanol, diethylene glycol monomethyl ether, diethylene glycol monoethyl ether, their mixtures with water or pure water. and if appropriate in the presence of a base, preferably of an alkaline earth metal or alkali metal or ammonium hydride. hydroxide, amide, alkoxide, acetate, carbonate or hydrogen carbonate, such as, for example, sodium hydride, sodium amide, sodium methoxide, sodium ethoxide, potassium tert-butoxide, sodium hydroxide, potassium hydroxide, ammonium hydroxide, sodium acetate, potassium acetate, calcium acetate, ammonium acetate, sodium carbonate, potassium carbonate, potassium hydrogen carbonate, sodium hydrogen carbonate or ammonium carbonate, or of a tertiary amine, such as trimethylamine, triethylamine, tributylamine, N,N-dimethylaniline, N,N-dimethyl-benzylamine, pyridine, N-methylpiperidine, N-methylmorpholine, N,N-dimethylaminopyridine, diazabicyclooctane (DABCO), diazabicyclononene (DBN) or diazabicycloundecene (DBU), at temperatures from −20° C. to 120° C., preferably at temperatures from −10° C. to 80° C.

Formula (V) provides a general definition of the arylacetic acid derivatives needed as starting substances for carrying out process c) according to the invention for the preparation of the acetals of the formula (IV). In this formula (V), $Q^1$ preferably or in particular has the meaning which has already been indicated as preferred or as particularly preferred for $Q^1$ in connection with the description of the compounds of the formula (Ia) according to the invention. $R^1$ and $R^2$ preferably have those meanings which have already been indicated as preferred in connection with the description of the compounds of the formula (IV).

The arylacetic acid derivatives of the formula (V) are known in some cases and/or can be prepared by known processes (compare, for example, J. Org. Chem. 1994, 203–13).

Arylacetic acid derivatives which are new and also a subject of the present application are those of the formula (Va)

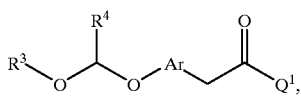

(Va)

in which $R^3$ and $R^4$ are identical or different and independently of one another represent alkyl and $Q^1$ has the meaning indicated above.

The arylacetic acid derivatives of the formula (Va) are obtained (process d) when hydroxy compounds of the general formula (VII)

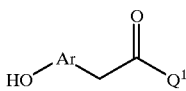

(VII)

in which $Q^1$ has the meaning indicated above, are reacted with vinyl ethers of the general formula (VIII)

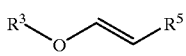

(VIII)

in which $R^3$ has the meaning indicated above and $R^5$ represents hydrogen or alkyl, if appropriate in the presence of a diluent, preferably of an aliphatic, alicyclic or aromatic hydrocarbon, such as, for example, petroleum ether, hexane, heptane, cyclohexane, methylcyclohexane, benzene, toluene, xylene or decal in; of a halogenated hydrocarbon, such as, for example, chlorobenzene, dichlorobenzene, dichloromethane, chloroform, tetrachloromethane, dichloroethane or trichloroethane; of an ether, such as diethyl ether, dilsopropyl ether, methyl t-butyl ether, methyl t-amyl ether, dioxane, tetrahydrofuran, 1,2-dimethoxyethane, 1,2-diethoxyethane or anisole or of a nitrile, such as acetonitrile, propionitrile, n- or i-butyronitrile or benzonitrile, and if appropriate in the presence of an acid, preferably of an inorganic or organic protonic or Lewis acid, or alternatively of a polymeric acid, such as, for example, hydrochloric acid, sulphuric acid, phosphoric acid, formic acid, acetic acid, trifluoroacetic acid, methanesulphonic acid, trifluoromethanesulphonic acid, toluenesulphonic acid, boron trifluoride (also as etherate), boron tribromide, aluminium trichloride, zinc chloride, iron(III) chloride, antimony pentachloride, acidic ion exchangers, acidic aluminas and acidic silica gel.

Formula (Va) provides a general definition of the new arylacetic acid derivatives. In this formula (Va), $Q^1$ preferably or in particular has those meanings which have already been indicated as preferred or as particularly preferred for $Q^1$ in connection with the description of the compounds of the formula (Ia) according to the invention. $R^3$ and $R^4$ are identical or different and independently of one another represent alkyl, preferably methyl or ethyl.

Formula (VII) provides a general definition of the hydroxy compounds needed for carrying out process d) according to the invention for the preparation of the compounds of the formula (Va) according to the invention. In this formula (VII), $Q^1$ preferably or in particular has the meaning which has already been indicated as preferred or as particularly preferred for $Q^1$ in connection with the description of the compounds of the formula (Ia) according to the invention.

The hydroxy compounds of the formula (VII) are known synthesis chemicals.

Formula (VIII) provides a general definition of the vinyl ethers furthermore needed for carrying out process d) according to the invention for the preparation of the compounds of the formula (Va) according to the invention. In this formula (VIII), $R^3$ preferably has the meaning which has been indicated as preferred or as particularly preferred for $R^3$ in connection with the description of the compounds of the formula (Va) according to the invention. $R^5$ represents hydrogen or alklyl, preferably hydrogen or methyl.

The vinyl ethers of the formula (VIII) are known synthesis chemicals.

Formula (III) provides a general definition of the thiadiazole derivatives furthermore needed as starting substances for carrying out process a) according to the invention. In this formula (III), $Ar^1$ preferably or in particular has the meaning which has already been indicated as preferred or as particularly preferred for $Ar^1$ in connection with the description of the compounds of the formula (Ia) according to the invention. X represents halogen, preferably fluorine or chlorine, or alkylsulphonyl or arylsulphonyl, preferably methylsulphonyl, benzylsulphonyl or tolylsulphonyl.

The thiadiazole derivatives of the formula (III) are known synthesis chemicals and/or can be prepared by known processes (compare, for example, J. Heterocyclic Chem. 30, 357 (1993)).

All inert organic solvents are suitable as diluents for carrying out process a) according to the invention. These preferably include aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, dichloromethane, chloroform, tetrachloromethane, dichloroethane or trichloroethane; ethers, such as diethyl ether, diisopropyl ether, methyl t-butyl ether, methyl t-amyl ether, dioxane, tetrahydrofuran, 1,2-dimethoxyethane, 1,2-diethoxyethane or anisole; ketones, such as acetone, butanone, methyl isobutyl ketone or cyclohexanone; nitrites, such as acetonitrile, propionitrile, n-or i-butyronitrile or benzonitrile; amides, such as N,N- dimethylformamide, N,N-dimethylacetamide, N-methylformanilide, N-methylpyrrolidone or hexamethylphosphoramide; esters such as methyl acetate or ethyl acetate; sulphoxides, such as dimethyl sulphoxide; sulphones, such as sulpholane; alcohols, such as methanol, ethanol, n- or i-propanol, n-, i-, sec- or tert-butanol, ethanediol, propane-1,2-diol, ethoxyethanol, methoxyethanol, diethylene glycol monomethyl ether, diethylene glycol monoethyl ether, mixtures thereof with water or pure water.

Process a) according to the invention is optionally carried out in the presence of a suitable acid acceptor. Those possible are all customary inorganic or organic bases. These include, for example, alkaline earth metal or alkali metal or ammonium hydrides. hydroxides, amides, alkoxides, acetates, carbonates or hydrogen carbonates, such as, for example, sodium hydride, sodium amide, sodium methoxide, sodium ethoxide, potassium tert-butoxide, sodium hydroxide, potassium hydroxide, ammonium hydroxide, sodium acetate, potassium acetate, calcium acetate, ammonium acetate, sodium carbonate, potassium carbonate, potassium hydrogen carbonate, sodium hydrogen carbonate or ammonium carbonate, and also tertiary amines, such as trimethylamine, triethylamine, tributylamine, N,N-dimethylaniline, N,N-dimethyl-benzylamine, pyridine, N-methylpiperidine, N-methylmorpholine, N,N-dimethylaminopyridine, diazabicyclooctane (DABCO), diazabicyclononene (DBN) or diazabicycloundecene (DBU).

When carrying out process a) according to the invention, the reaction temperatures can be varied within a relatively wide range. In general, the reaction is carried out at temperatures from 0° C. to 150° C., preferably at temperatures from 0° C. to 80° C.

To carry out process a) according to the invention for the preparation of the compounds of the formula (Ia), in general 0.2 to 5 mol, preferably 0.5 to 2 mol, of thiadiazole derivative of the general formula (III) are employed per mole of the hydroxyaryl compounds of the general formula (II).

Process a) according to the invention is in general carried out under normal pressure. However, it is also possible to work at elevated or reduced pressure—in general between 0.1 bar and 10 bar.

The reaction is carried out and worked up, and the reaction products are isolated by known processes (cf. also the Preparation Examples).

The active compounds according to the invention have a potent microbicidal action and can be employed in practice for controlling undesired microorganisms. The active compounds are suitable for use as plant protection agents, in particular as fungicides.

Fungicidal agents are employed in plant protection for controlling Plasmodiophoromycetes, Oomycetes, Chytridiomycetes, Zygomycetes, Ascomycetes, Basidiomycetes and Deuteromycetes.

Bactericidal agents are employed in plant protection for controlling Pseudomonadaceae, Rhizobiaceae, Enterobacteriaceae, Corynebacteriaceae and Streptomycetaceae.

Some causative organisms of fungal and bacterial diseases which come under the generic names listed above may be mentioned as examples, but not by way of limitation:

Xanthomonas species. such as, for example, *Xanthomonas campestris* pv. oryzae;
Pseudomonas species, such as, for example, *Pseudomonas syringae* pv. lachrymans;
Erwinia species, such as, for example, *Erwinia amylovora;*
Pythium species, such as, for example, *Pythium ultimum;*
Phytophthora species, such as, for example, *Phytophthora infestans;*
Pseudoperonospora species, such as, for example, *Pseudoperonospora humuli* or *Pseudoperonospora cubensis;*
Plasmopara species, such as, for example, *Plasmopara viticola;*
Bremia species, such as, for example, *Bremia lactucae;*
Peronospora species, such as, for example, *Peronospora pisi* or *P. brassicae;*
Erysiphe species, such as, for example, *Erysiphe graminis;*
Sphaerotheca species, such as, for example, *Sphaerotheca fuliginea;*
Podosphaera species, such as, for example, *Podosphaera leucotricha;*
Venturia species, such as, for example, *Venturia inaequalis;*
Pyrenophora species, such as, for example, *Pyrenophora teres* or *P. graminea* (conidia form: Drechslera, syn: Helminthosporium);
Cochliobolus species, such as, for example, *Cochliobolus sativus* (conidia form:
Drechslera, syn: Helminthosporium);
Uromyces species, such as, for example, *Uromyces appendiculatus;*
Puccinia species, such as, for example, *Puccinia recondita;*
Sclerotinia species, such as. for example, *Sclerotinia sclerotiorum;*
Tilletia species, such as, for example, *Tilletia caries;*
Ustilago species, such as, for example, *Ustilago nuda* or *Ustilago avenae;*
Pellicularia species, such as, for example, *Pellicularia sasakii;*
Pyricularia species, such as, for example, *Pyricularia oryzae;*
Fusarium species, such as, for example, *Fusarium culmorum;*
Botrytis species, such as, for example, *Botrytis cinerea;*
Septoria species, such as, for example, *Septoria nodorum;*
Leptosphaeria species, such as, for example, *Leptosphaeria nodorum;*
Cercospora species, such as, for example, *Cercospora canescens;*
Alternaria species, such as, for example, *Alternaria brassicae;* and
Pseudocercosporella species, such as, for example, *Pseudocercosporella herpotrichoides.*

The good toleration, by plants, of the active compounds, at the concentrations required for controlling plant diseases, permits treatment of above-ground parts of plants, of vegetative propagation stock and seeds, and of the soil.

The active compounds according to the invention can be employed here to particularly good effect for controlling cereal diseases, such as, for example, against Erysiphe or Leptosphaeria species, or diseases in viticulture, fruit- and vegetable growing, such as, for example, against Plasmopara, Uncinula, Sphaerotheca or Venturia species, or alternatively rice diseases, such as, for example, Pyricularia species. The active compounds according to the invention additionally show a particularly potent and wide in vitro action.

Depending on their particular physical and/or chemical properties, the active compounds can be converted to the customary formulations, such as solutions, emulsions, suspensions, powders, foams, pastes, granules, aerosols, very fine capsules in polymeric substances and in coating compositions for seed, as well as ULV cold mist and warm mist formulations.

These formulations are produced in a known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at ambient temperature and under atmospheric pressure, for example aerosol propellants, such as halogenated hydrocarbons as well as butane, propane, nitrogen and carbon dioxide; as solid carriers there are suitable: for example ground natural minerals, such as kaolins, argillaceous earths, talc, chalk, quartz, attapulgite, montmorillonite or diatomaceous earth, and ground synthetic minerals, such as highly-disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention, as such or in their formulations, can also be used as a mixture with known fungicides, bactericides, acaricides, nematicides or insecticides, for example to widen the spectrum of action or to prevent the build-up of resistance. In many cases, synergistic effects are obtained, i.e. the activity of the mixture is greater than the activity of the individual components.

Synergistic actions are observed here in many cases.

Examples of particularly advantageous mixture components are the following compounds:

Fungicides 2-aminobutane; 2-anilino-4-methyl-6-cyclopropyl-pyrimidine; 2', 6'-dibromo-2-methyl-4'-trifluoromethoxy-4'-trifluoro-methyl-1,3-thiazole-5-carboxanilide; 2,6-dichloro-N-(4-trifluoromethyl)benzamide; (E)-2-methoxyimino-N-methyl-2-(2-phenoxy-phenyl)acetamide; 8-hydroxyquinoline sulphate; methyl (E)-2-{2-[6-(2-cyano-phenoxy)pyrimidin-4-yloxy]-phenyl }-3-methoxycrylate; methyl (E)-methoximino[alpha-(o-tolyloxy)-o-tolyl]acetate;

2-phenylphenol (OPP), aldimorph, ampropylfos, anilazine, azaconazole, benalaxyl, benodanil, benomyl, binapacryl, biphenyl, bitertanol, blasticidin-S, bromuconazole, bupirimate, buthiobate, calcium polysulphide, captafol, captan, carbendazim, carboxin, quinomethionate, chloroneb, chloropicrin, chlorothalonil. chlozolinate, cufraneb, cymoxanil, cypro-conazole, cyprofuram, dichlorophen, diclobutrazol, diclofluanid, diclomezin, dicloran, diethofencarb, difenoconazole, dimethirimol, dimethomorph, diniconazole, dinocap, diphenylamine, dipyrithion, ditalimfos, dithianon, dodine, drazoxolon, edifenphos, epoxyconazole, ethirimol, etridiazole, fenarimol, fenbuconazole, fenfuram, fenitropan, fenpiclonil, fenpropidin, fenpropimorph, fentin acetate, fentin hydroxide, ferbam, ferimzone, fluazinam, fludioxonil, fluoromide, fluquinconazole, flusilazole, flusulfamide, flutolanil, flutriafol, folpet, fosetyl-aluminium, fthalide, fuberidazole, furalaxyl, furmecyclox, guazatine, hexachlorobenzene, hexaconazole, hymexazol, imazalil, imibenconazole, iminoctadine, iprobenfos (IBP), iprodione, isoprothiolane, kasugamycin, copper preparations such as: copper hydroxide, copper naphthenate, copper oxychloride, copper sulphate, copper oxide, oxine-copper and Bordeaux mixture, mancopper, mancozeb, maneb, mepanipyrim, mepronil, metalaxyl, metconazole, methasulfocarb, methfuroxam, metiram, metsulfovax, myclobutanil, nickel dimethyldithiocarbamate, nitrothal-isopropyl, nuarimol, ofurace, oxadixyl, oxamocarb, oxycarboxin, pefurazoate, penconazole, pencycuron, phosdiphen, pimaricin, piperalin, polyoxin, probenazole, prochloraz, procymidone, propamocarb, propiconazole, propineb, pyrazophos, pyrifenox, pyrimethanil, pyroquilon, quintozene (PCNB), sulphur and sulphur preparations, tebuconazole, tecloftalam, tecnazene, tetraconazole, thiabendazole, thicyofen, thiophanate-methyl, thiram, tolclophos-methyl, tolylfluanid, triadimefon, triadimenol, triazoxide, trichlamide, tricyclazole, tridemorph, triflumizole, triforine, triticonazole, validamycin A, vinclozolin, zineb, ziram Bactericides bronopol, dichlorophen, nitrapyrin, nickel dimethyldithiocarbamate, kasugamycin, octhilinone, furanecarboxylic acid, oxytetracyclin, probenazole, streptomycin, tecloftalam, copper sulphate and other copper preparations.

Insecticides/Acaricides/Nematicides abamectin, acephate, acrinathrin, alanycarb, aldicarb, alphamethrin, amitraz, avernectin, AZ 60541, azadirachtin, azinphos A, azinphos M, azocyclotin, Bacillus thuringiensis, 4-bromo-2-(4-chlorophenyl)-1-(ethoxymethyl)-5-(trifluoromethyl)-1H-pyrrole-3-carbonitrile, bendiocarb, benfuracarb, bensultap, beta-cyfluthrin, bifenthrin, BPMC, brofenprox, bromophos A, bufencarb, buprofezin, butocarboxin, butylpyridaben, cadusafos, carbaryl, carbofuran, carbophenothion, carbosulfan, cartap, chloethocarb, chlorethoxyfos, chlorfenvinphos, chlorfluazuron, chlormephos, N-[(6-chloro-3-pyridinyl)-methyl ]-N'-cyano-N-methyl-ethaneimidamide, chlorpyrifos, chlorpyrifos M, cis-resmethrin, clocythrin, clofentezine, cyanophos, cycloprothrin, cyfluthrin, cyhalothrin, cyhexatin, cypermethrin, cyromazine, deltamethrin, demeton-M, demeton-S, demeton-S-methyl, diafenthiuron, diazinon, dichlofenthion, dichlorvos, dicliphos, dicrotophos, diethion, diflubenzuron, dimethoate, dimethylvinphos, dioxathion, disulfoton, edifenphos, emamectin, esfenvalerate, ethiofencarb, ethion, ethofenprox, ethoprophos, etofenprox, etrimphos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, fluazuron, flucycloxuron, flucythrinate, flufenoxuron, flufenprox, fluvalinate, fonophos, formothion, fosthiazate, fubfenprox, furathiocarb, HCH, heptenophos, hexaflumuron, hexythiazox, imidacloprid, iprobenfos, isazofos, isofenphos, isoprocarb, isoxathion, ivermectin, lambda-cyhalothrin, lufenuron, malathion, mecarbam, mevinphos, mesulfenphos, metaldehyde, methacrifos, methamidophos, methidathion, methiocarb, methomyl, metolcarb, milbemectin, monocrotophos, moxidectin, naled, NC 184, nitenpyram, omethoate, oxamyl, oxydemethon M, oxydeprofos, parathion A, parathion M, permethrin, phenthoate, phorate, phosalone, phosmet, phosphamidon, phoxim, pirimicarb, pirimiphos M. pirimiphos A, profenofos, promecarb, propaphos, propoxur, prothiofos, prothoate, pymetrozin, pyrachlophos, pyraclofos, pyrachlophos, pyridaphenthion, pyresmethrin, pyreth lrum, pyridaben, pyrimidifen, pyriproxifen, quinalphos, salithion, sebufos, silafluofen, sulfotep, sulprofos, tebufenozide, tebufenpyrad, tebupirimiphos, teflubenzuron, tefluthrin, temephos, terbam, terbufos, tetrachlorvinphos, thiafenox, thiodicarb, thiofanox, thiomethon, thionazin, thuringiensin, tralomethrin, triarathen, triazophos, triazuron, trichlorfon, triflumuron, trimethacarb, vamidothion, XMC, xylylcarb, YI 5301/5302, zetamethrin.

A mixture with other known active compounds, such as herbicides, or with fertilizers and growth regulators is also possible.

The active compounds according to the invention are used as such or in the form of their commercially available formulations or the use forms prepared therefrom, such as ready-to-use solutions, suspensions, wettable powders, pastes, soluble powders, dusts and granules. They are used in the customary manner, for example by watering, spraying, atomizing, scattering, foaming, brushing on and the like. It is furthermore possible to apply the active compounds by the ultra-low volume method or to inject the active compound preparation or the active compound itself into the soil. The seeds of the plants can also be treated.

In the treatment of parts of plants, the active compound concentrations in the use forms can be varied within a substantial range. They are, in general, between 1 and 0.0001% by weight, preferably between 0.5 and 0.001% by weight.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001to 00.2% by weight, are required at the place of action.

PREPARATION EXAMPLES

Example 1

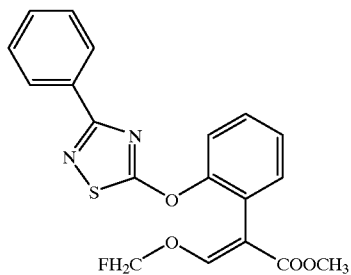

Process a)

A solution of 3.2 g (0.005 mol) of 3-phenyl-5-methanesulphonyl-1,2,4-thiadiazole and 2.3 g of methyl 2-(2-hydroxyphenyl)-3-fluoromethoxy-acrylate in 10 ml of dry dimethylformamide is treated at 0° C. with 0.2 g (0.005 mol) of 80% strength sodium hydride in mineral oil. The mixture is stirred for 4 hours at this temperature, and for a further 18 hours without cooling, and then concentrated. The residue is taken up using ethyl acetate, the solution is washed with water, and the organic phase is dried over sodium sulphate and concentrated again. The crude product is chromatographed on silica gel using hexane/acetone (7:3). 1.3 g (67% of theory) of methyl 2-[2-(3-phenyl-1,2,4-thiadiazol-5-yloxy)-phenyl]-3-fluoromethoxy-acrylate are obtained as a yellow, highly viscous oil.

$^1$H-NMR (CDCl$_3$, TMS): δ=5.4 (d, 2H) ppm.

Example 2

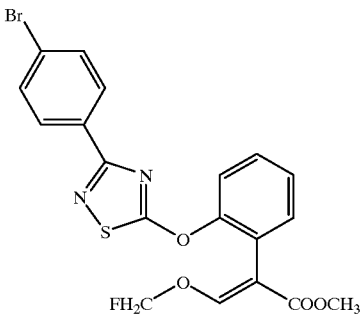

Process a)

A solution of 3.2 g (0.01 mol) of 3-phenyl-5-toluenesulphonyl-1,2,4-thiadiazole and 1.1 g of methyl 2-(2-hydroxyphenyl)-3-fluoromethoxy-acrylate in 30 ml of dry dimethylformamide is treated at 0° C. with 0.3 g (0.01 mol) of 80% strength sodium hydride in mineral oil. The mixture is stirred for 3 days without cooling and then concentrated. The residue is taken up using ethyl acetate, the solution is washed with water, and the organic phase is dried over sodium sulphate and concentrated again. The crude product is chromatographed on silica gel using hexane/acetone (9:1). 2.8 g (60% of theory) of methyl 2-{2-[3-(4-bromophenyl)-1,2,4-thiadiazol-5-yloxy]-phenyl}-3-fluoromethoxy-acrylate are obtained as a yellow, highly viscous oil.

$^1$H-NMR (CDCl$_3$, TMS): δ=5.4 (d, 2H) ppm.

Preparation of the Starting Substance

Example II-1:

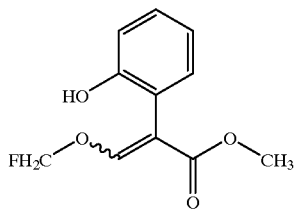

Process b)

6.2 g (0.02 mol) of methyl 2-[2-(tetrahydropyran-2-yloxy)-phenyl]-3-fluoromethoxy-acrylate are stirred in 30 ml of methanol at 20° C for 18 hours with 0.5 g of acidic ion exchanger. The ion exchanger is filtered off and the filtrate is concentrated. The residue is chromatographed on silica gel using hexane/acetone (7:3). 3.3 g (73% of theory) of methyl 2-(2-hydroxyphenyl)-3-fluoromethoxy-acrylate are obtained as a pale yellow, viscous oil.

$^1$H-NMR (CDCl$_3$, TMS): δ=5.4 (d, 2H) ppm.

Ethyl 2-(2-hydroxyphenyl)-3-fluoromethoxy-acrylate is also obtained analogously to Example II-1 and corresponding to the general description of preparation process b) according to the invention.

¹H-NMR (CDCl₃, TMS): δ=1.30 (t, 3H); 4.32 (q, 2H) ppm.

Preparation of the Precursor

Example IV-1:

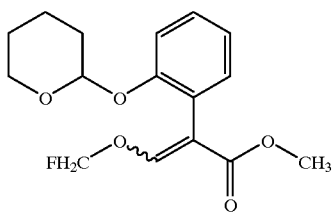

Process c)

1.5 g of 80% strength sodium hydride in mineral oil are added in portions at 20° C. with stirring to a solution of 12.5 g (60 mmol) of methyl 2-[2-(tetrahydropyran-2-yloxy)-phenyl]-acrylate and 30 g of methyl formate in 150 ml of dry dimethylformamide in a three-necked flask having an attached condenser. After approximately one hour, the exothermic reaction commences with foaming. The temperature is kept at 40° C. for 3 hours. The mixture is cooled to 0–5° C. and treated successively with 4.8 g (0.05 mol) of methanesulphonic acid and in portions with 13.8 g (0.1 mol) of potassium carbonate. The temperature of the cooling fluid in the condenser, as well as the temperature of the reaction mixture, is then adjusted to 0° C. Using a syringe, 6.8 g (0.06 mol) of bromofluoromethane are added and the mixture is stirred overnight at 0–5° C. The reaction mixture is stirred for a further 24 hours without cooling. The temperature of the cooling fluid is kept at approximately 0° C. The mixture is concentrated, the residue is taken up using ethyl acetate, the solution is washed with water, and the organic phase is dried over sodium sulphate and concentrated again. The residue is chromatographed on silica gel using hexane/acetone (7:3). 11.6 g (75% of theory) of methyl 2-[2-(tetrahydropyran-2-yloxy)-phenyl]-3-fluoromethoxy-acrylate are obtained.

¹H-NMR (CDCl₃, TMS): δ=5.5 (d, 2H) ppm.

The compounds of the formula (Ia) according to the invention, shown in Table 1 below, are also obtained analogously to Examples (1–2), and corresponding to the general description of the preparation process according to the invention:

TABLE 1

(Ia)

| Ex.-No. | Ar¹ | Q¹ | Physical data | Isomers |
|---|---|---|---|---|
| 3 | H₃CO—⟨ ⟩— | —OCH₃ | NMR: 5.4 (d, 2H) | E-isomer |
| 4 | H₃C—⟨ ⟩— | —OCH₃ | NMR: 5.4 (d, 2H) | E-isomer |
| 5 | Cl—⟨ ⟩— | —OCH₃ | NMR: 5.4 (d, 2H) | E-isomer |
| 6 | F—⟨ ⟩— | —OCH₃ | NMR: 5.4 (d, 2H) | E-isomer |
| 7 | H₃C—⟨ ⟩— (meta) | —OCH₃ | NMR: 5.4 (d, 2H) | E-isomer |

TABLE 1-continued
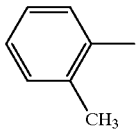
(Ia)
| Ex.-No. | Ar¹ | Q¹ | Physical data | Isomers |
|---|---|---|---|---|
| 8 | 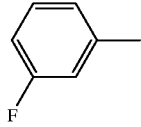 | —OCH₃ | NMR: 5.4 (d, 2H) | E-isomer |
| 9 | 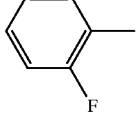 | —OCH₃ | | E-isomer |
| 10 | 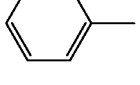 | —OCH₃ | | E-isomer |
| 11 | 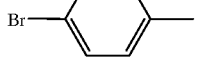 | —OC₂H₅ | NMR: 5.42 (d, 2H); 7.63 (s, 1H) | E-isomer |
| 12 | 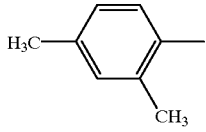 | —OC₂H₅ | NMR 5.42 (d, 2H); 7.65 (s, 1H) | E-isomer |
| 13 | 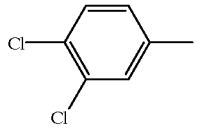 | —OCH₃ | | E-isomer |
| 14 | 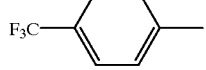 | —OCH₃ | | E-isomer |
| 15 | 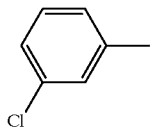 | —OCH₃ | | E-isomer |
| 16 |  | —OC₂H₅ | NMR 5.39 (d, 2H); 7.65 (s, 1H) | E-isomer |

TABLE 1-continued (Ia)

[Structure: Ar¹ connected to 1,2,4-thiadiazole ring with O linker to phenyl ring bearing C(=COQ¹)(OCH₂F) group]

| Ex.-No. | Ar¹ | Q¹ | Physical data | Isomers |
|---|---|---|---|---|
| 17 | 2-Cl-phenyl | —O—CH₃ | NMR: 5.40 (d, 2H); | E-isomer |
| 18 | 2-Br-phenyl | —O—CH₃ | NMR: 5.40 (d, 2H); | E-isomer |
| 19 | 2-OCH₃-phenyl | —OCH₃ | NMR: 5.40 (d, 2H); | E-Isomer |
| 20 | phenyl | —OCH₃ | $^1$H-NMR: 5.5 (d, 2H); | Z-isomer |
| 21 | 4-Br-phenyl | —OCH₃ | $^1$H-NMR: 5.5 (d, 2H); | Z-isomer |
| 22 | 4-Cl-phenyl | —OCH₃ | Fp: 113° C. | Z-isomer |
| 23 | 3-Cl-phenyl | —OCH₃ | $^1$H-NMR 5.4 (d, 2H); | E-isomer |

Use Examples

Example: A

Plasmopara test (vine)/protective

Solvent: 4.7 parts by weight of acetone

Emulsifier: 0.3 part by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound. After the spray coating has dried on, the plants are inoculated with an aqueous spore suspension of *Plasmopara viticola* and then remain in a humidity chamber at 20 to 22° C. and 100% relative atmospheric humidity for 1 day. The plants are then placed in a greenhouse at 21° C. and about 90% atmospheric humidity for 5 days. The plants are then moistened and placed in a humidity chamber for 1 day.

Evaluation is carried out 6 days after the inoculation.

In this test, for example, the following compound (2) of the Preparation Examples shows an efficacy of 100% at an active compound concentration of 100 ppm.

TABLE A

Plasmopara test (vine)/protective

| Active compound | Efficacy in % of the untreated control at an active compound concentration of 100 ppm |
|---|---|
| 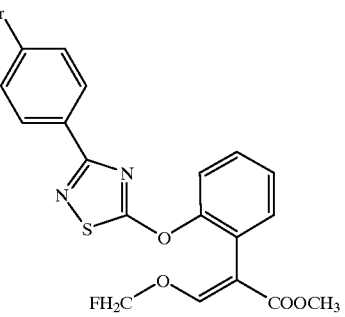<br>(2) (according to the invention) | 100 |

Example: B

Uncinula test (vine)/protective

Solvent: 4.7 parts by weight of acetone

Emulsifier: 0.3 part by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound. After the spray coating has dried on, the plants are dusted with conidia of the fungus *Uncinula necator*. The plants are then placed in a greenhouse at 23 to 24° C. and a relative atmospheric humidity of about 75%.

Evaluation is effected 14 days after the inoculation.

In this test, for example, the following compound (2) of the Preparation Examples shows an efficacy of 100% at an active -compound concentration of 10 ppm.

TABLE B

Uncinula test (vine)/protective

| Active compound | Efficacy in % of the untreated control at an active compound concentration of 25 ppm |
|---|---|
| 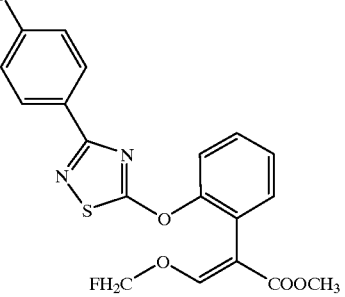<br>(2) (according to the invention) | 100 |

Example: C

Sphaerotheca test (cucumber)/protective

Solvent: 4.7 parts by weight of acetone

Emulsifier: 0.3 part by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound. After the spray coating has dried on, the plants are dusted with conidia of the fungus *Sphaerotheca fuliginea*.

The plants are then placed in a greenhouse at 23 to 24° C. and at a relative atmospheric humidity of about 75%.

Evaluation is carried out 10 days after the inoculation.

In this test, for example, the following compound (2) of the Preparation Examples shows an efficacy of 100% at an active compound concentration of 100 ppm.

TABLE C

Sphaerotheca test (cucumber)/protective

| Active compound | Efficacy in % of the untreated control at an active compound concentration of 100 ppm |
|---|---|
| 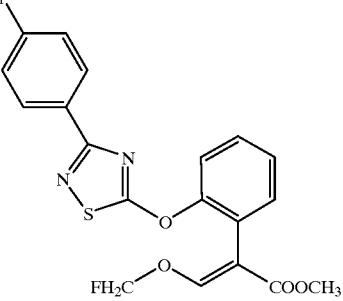<br>(2) (according to the invention) | 100 |

Example D

Venturia test (apple)/protective

Solvent: 4.7 parts by weight of acetone

Emulsifier: 0.3 part by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound. After the spray coating has dried on, the plants are inoculated with an aqueous conidia suspension of the apple scab causative organism *Venturia inaequalis* and then left in an incubation cabin at 20° C. and 100% relative atmospheric humidity for 1 day.

The plants are then placed in a greenhouse at 20° C. and a relative atmospheric humidity of about 70%.

Evaluation is carried out 12 days after the inoculation.

In this test, for example, the following compound (2) of the Preparation Examples shows an efficacy of 100% at an active compound concentration of 10 ppm.

TABLE D

Venturia test (apple)/protective

| Active compound | Efficacy in % of the untreated control at an active compound concentration of 10 ppm |
|---|---|
| [Structure: 4-bromophenyl-thiadiazole-O-phenyl-C(=CHOCH2F)COOCH3]<br>(2) (according to the invention) | 100 |

TABLE E

Erysiphe test (barley)/protective

| Active compound | Efficacy in % of the untreated control at an active compound concentration of 250 g/ha |
|---|---|
| [Structure: 4-bromophenyl-thiadiazole-O-phenyl-C(=CHOCH2F)COOCH3]<br>(2) (according to the invention) | 81 |

Example E

Erysiphe test (barley)/protective

Solvent: 10 parts by weight of N-methyl-pyrrolidone

Emulsifier: 0.6 part by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at given application rate.

After the spray coating has dried on, the plants are dusted with spores of *Erysiphe graminis* f.sp. hordei.

The plants are placed in a greenhouse at a temperature of about 20° C. and a relative atmospheric humidity of about 80%, in order to promote the development of powdery mildew pustules.

Evaluation is carried out 7 days after the inoculation.

In this test, for example, the following compound (2) shows an efficacy of 81% at an active compound application rate of 250 g/ha.

Example F

*Leptosphaena nodorum* test (wheat)/protective

Solvent: 10 parts by weight of N-methyl-pyrrolidone

Emulsifier: 0.6 part by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound.

After the spray coating has dried on, the plants are sprayed with a spore suspension of *Leptosphaeria nodorum*. The plants remain for 48 hours in an incubation cabin at 20° C. and 100% relative atmospheric humidity.

The plants are placed in a greenhouse at a temperature of about 15° C. and a relative atmospheric humidity of about 80%.

Evaluation is effected 10 days after the inoculation.

In this test, for example, the following compound of the Preparation Examples (2) shows an efficacy of 88% at an active compound application rate of 250 g/ha.

TABLE F

_Leptosphaeria nodorum_ test (wheat)/protective

| Active compound | Efficacy in %, relative of the untreated control, at an active compound application rate of 250 g/ha |
|---|---|
| (2) (according to the invention) [structure: 4-bromophenyl-thiadiazolyl-O-phenyl with FH$_2$C-O-CH=C(COOCH$_3$)] | 88 |

We claim:

1. A compound of the formula (I)

(I) [structure: Ar-thiadiazolyl-O-phenyl with FH$_2$C-O-CH=C(COQ)]

in which

Ar represents substituted aryl and

Q represents unsubstituted or substituted alkoxy.

2. A compound of the formula (I) according to claim 1, in which

Ar represents mono- to trisubstituted phenyl or mono- to tetrasubstituted naphthyl, the substituents being:

halogen, cyano, nitro; alkyl, alkoxy, alkylthio, alkylsulphinyl or alkylsulphonyl, each of which is straight-chain or branched and has 1 to 6 carbon atoms; alkenyl, alkenyloxy or alkinyloxy, each of which is straight-chain or branched and has 2 to 6 carbon atoms; halogenoalkyl, halogenoalkoxy, halogenoalkylthio, halogenoalkylsulphinyl or halogenoalkylsulphonyl, each of which is straight-chain or branched and has 1 to 6 carbon atoms and 1 to 13 identical or different halogen atoms, halogenoalkenyl or halogenoalkenyloxy, each of which is straight-chain or branched and has 2 to 6 carbon atoms and 1 to 11 identical or different halogen atoms; alkylamino, dialkylamino, alkylcarbonyl, alkylcarbonyloxy, alkoxycarbonyl, alkylsulphonyloxy, hydroximinoalkyl or alkoximinoalkyl, each of which is straight-chain or branched and has 1 to 6 carbon atoms in the individual alkyl moieties; alkylene or dioxyalkylene, each having 1 to 6 carbon atoms, and each of which is divalent and is unsubstituted, mono- or polysubstituted, identically or differently, by at least one of halogen straight-chain or branched alkyl having 1 to 4 carbon atoms or straight-chain or branched halogenoalkyl having 1 to 4 carbon atoms and 1 to 9 identical or different halogen atoms; or cycloalkyl having 3 to 6 carbon atoms, and Q represents $C_1$–$C_6$-alkoxy which is unsubstituted or substituted by halogen or $C_1$–$C_4$-alkoxy.

3. A compound of the formula (I) according to claim 1, in which

Ar represents phenyl which is mono- or disubstituted, identically or differently, the substituents being:

fluorine, chlorine, bromine, cyano, methyl, ethyl, n- or i-propyl, n-, i-, s- or t-butyl, cyclopropyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, trifluoromethylthio, difluorochloromethylthio, trifluoromethylsulphinyl or trifluoromethylsulphonyl, methoxycarbonyl, ethoxycarbonyl, methoximinomethyl, ethoximinomethyl, methoximinoethyl, ethoximinoethyl, or methylenedioxy, ethylenedioxy, each of which is divalent and is unsubstituted or mono- to tetrasubstituted, identically or differently, by fluorine, chlorine, methyl, trifluoromethyl or ethyl and Q represents methoxy or ethoxy.

4. Process for the preparation of a compound of the formula (Ia)

(Ia) [structure: Ar$^1$-thiadiazolyl-O-phenyl with FH$_2$C-O-CH=C(COQ$^1$)]

in which

Ar$^1$ represents unsubstituted or substituted aryl and

Q$^1$ represents unsubstituted or substituted alkoxy, comprising reacting a hydroxyaryl compound of the formula (II)

(II) [structure: HO-phenyl with FH$_2$C-O-CH=C(COQ$^1$)]

in which

Q$^1$ has the meaning indicated above, with a thiadiazole derivative of the formula (III)

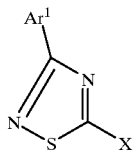

(III)

in which
- Ar$^1$ has the meaning indicated above and
- X represents halogen, alkylsulphonyl or arylsulphonyl, in the absence or presence of an acid acceptor and in the absence or presence of a diluent.

5. A pesticide comprising a pesticidally effective amount of at least one compound of the formula (I) according to claim 1 and a diluent.

6. Method of combatting pests, comprising applying a pesticidally effective amount of at least one compound of the formula (I) according to claim 1 to the pests or their habitat or to an area from which one desires to exclude such pests.

7. Process for the production of a pesticide comprising mixing at least one compound of the formula (I) according to claim 1 with at least one of extenders or surface-active agents.

8. A compound of the formula (Va)

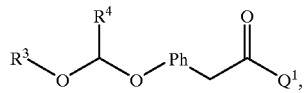

(Va)

in which
- R$^3$ and R$^4$ are identical or different and independently of one another represent alkyl and Q$^1$ has the meanings indicated in claim 4.

* * * * *

UNITED STATES PATENT AND TRADEMARK OFFICE
CERTIFICATE OF CORRECTION

PATENT NO. : 6,031,107
DATED : February 29, 2000
INVENTOR(S) : Ulrich HEINEMANN, et al.

It is certified that error appears in the above-indentified patent and that said Letters Patent is hereby corrected as shown below:

Column 26, line 1, after "halogen" insert --or--.

Signed and Sealed this

Seventeenth Day of April, 2001

Attest:

NICHOLAS P. GODICI

Attesting Officer     Acting Director of the United States Patent and Trademark Office